US011298035B2

(12) United States Patent
Huijbregts et al.

(10) Patent No.: US 11,298,035 B2
(45) Date of Patent: Apr. 12, 2022

(54) METHOD AND APPARATUS FOR MEASURING BLOOD PRESSURE

(71) Applicant: KONINKLIJKE PHILIPS N.V., Eindhoven (NL)

(72) Inventors: Laurentia Johanna Huijbregts, Eindhoven (NL); Rick Bezemer, Amsterdam (NL); Paul Aelen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1125 days.

(21) Appl. No.: 15/558,772

(22) PCT Filed: Feb. 25, 2016

(86) PCT No.: PCT/EP2016/053898
§ 371 (c)(1),
(2) Date: Sep. 15, 2017

(87) PCT Pub. No.: WO2016/146356
PCT Pub. Date: Sep. 22, 2016

(65) Prior Publication Data
US 2018/0070837 A1   Mar. 15, 2018

(30) Foreign Application Priority Data

Mar. 17, 2015   (EP) .................................... 15159388

(51) Int. Cl.
A61B 5/00   (2006.01)
A61B 5/021   (2006.01)
(Continued)

(52) U.S. Cl.
CPC ........ A61B 5/02233 (2013.01); A61B 5/0261 (2013.01); A61B 5/0295 (2013.01);
(Continued)

(58) Field of Classification Search
CPC . A61B 5/021; A61B 5/02416; A61B 5/02233; A61B 5/02116; A61B 5/0231;
(Continued)

(56) References Cited

U.S. PATENT DOCUMENTS 8,814,800 B2   8/2014   Fortin et al.
8,825,428 B2   9/2014   Addison et al.
(Continued)

FOREIGN PATENT DOCUMENTS

CN   1582845 A   2/2005
CN   1672631 A   9/2005
CN   103637788 A   3/2014

OTHER PUBLICATIONS

Wesseling, et al., "Physiocal, Calibrating Finger Vascular Physiology for Finapres", Homeostasis, vol. 36, No. 2-3, 1995, pp. 67-82.
(Continued)

Primary Examiner — Patricia J Park

(57) ABSTRACT

According to an aspect, there is provided an apparatus for measuring the blood pressure, BP, of a user, the apparatus comprising a volume-clamp BP monitoring device that comprises a first pressure device for applying pressure to a first part of the body of the user, a first photoplethysmogram, PPG, sensor for obtaining a first PPG signal from the first part of the body of the user, and a control unit that is configured to analyse the first PPG signal and to control the pressure of the first pressure device; wherein the control unit is configured to adjust the pressure of the first pressure device to maintain the first PPG signal at a constant level and to determine the BP of the user from the pressure of the first pressure device; and a second sensor, separate from the first PPG sensor, for measuring a physiological characteristic of the user in a second part of the body of the user, wherein the second part of the body is separate from the first part of the body; wherein the apparatus is configured to analyse the
(Continued)

measured physiological characteristic to determine a measure of the blood perfusion in the second part of the body of the user, and to determine whether to perform a recalibration of the volume-clamp BP monitoring device on the basis of changes in the blood perfusion.

13 Claims, 6 Drawing Sheets

(51) Int. Cl.
| | |
|---|---|
| *A61B 5/02* | (2006.01) |
| *A61B 5/1455* | (2006.01) |
| *A61B 5/022* | (2006.01) |
| *A61B 5/026* | (2006.01) |
| *A61B 5/0225* | (2006.01) |
| *A61B 5/0295* | (2006.01) |

(52) U.S. Cl.
CPC ...... *A61B 5/02116* (2013.01); *A61B 5/02255* (2013.01); *A61B 5/6838* (2013.01); *A61B 5/02007* (2013.01); *A61B 5/02241* (2013.01); *A61B 2560/0223* (2013.01)

(58) Field of Classification Search
CPC ................ A61B 5/0259; A61B 5/6838; A61B 2560/0223
See application file for complete search history.

(56) References Cited

U.S. PATENT DOCUMENTS

| | | | |
|---|---|---|---|
| 8,660,799 | B2 | 10/2014 | Chang et al. |
| 2005/0283083 | A1 | 12/2005 | Lee et al. |
| 2011/0105918 | A1* | 5/2011 | Fortin ............... A61B 5/0059 600/493 |
| 2011/0245690 | A1* | 10/2011 | Watson ............... A61B 5/022 600/485 |
| 2012/0136605 | A1 | 5/2012 | Addison et al. |
| 2012/0150002 | A1 | 6/2012 | Shelley et al. |
| 2013/0165780 | A1 | 6/2013 | Tamada |
| 2014/0257062 | A1* | 9/2014 | Masin ............... A61B 5/02141 600/324 |
| 2016/0007863 | A1* | 1/2016 | Ward ............... A61M 16/0003 600/324 |
| 2016/0058312 | A1* | 3/2016 | Han ....................... G01N 21/55 600/473 |

OTHER PUBLICATIONS

Fortin, et al., "Continuous non-invasive blood pressure monitoring using concentrically interlocking control loops", Computers in Biology and Medicine, vol. 36, No. 9, Sep. 1, 2006, pp. 941-957.
Hennig, et al., "Continuous blood pressure measurement using pulse transit time", Somnologie, Blackwell Wissenschaft, DE, vol. 17, No. 2, Jun. 6, 2013, pp. 104-110.

* cited by examiner

METHOD AND APPARATUS FOR MEASURING BLOOD PRESSURE

This application is the U.S. National Phase application under 35 U.S.C. § 371 of International Application No. PCT/EP2016/053898, filed on Feb. 25, 2016, which claims the benefit of European Application No. 15159388.6, filed Mar. 17, 2015. These applications are hereby incorporated by reference herein.

TECHNICAL FIELD OF THE INVENTION

The invention relates to the measurement of blood pressure using a volume-clamp blood pressure method, and in particular relates to improving the calibration of a system that uses the volume-clamp method.

BACKGROUND TO THE INVENTION

Arterial blood pressure (BP) is one of the most important vital signs and is widely used in clinical practice. One way to continuously measure blood pressure is using the so-called "volume clamp" method, which makes use of a PPG sensor and an inflatable cuff held around a finger or other body part. The cuff is continuously pressurised to follow the pressure in the finger artery using a closed-loop control system. The principle behind a volume-clamp BP monitoring device is that the diameter of the artery should be kept constant. Changes in the diameter of the artery can be measured with a plethysmographic sensor, of which a photoplethysmographic (PPG) sensor is the most commonly used.

One problem with measuring the blood pressure in this way is that changes in the blood perfusion (i.e. blood delivery) to the finger, for example, due to temperature-related vasoregulation, certain disease states, or certain medications, may change the relationship between the PPG signal and the blood pressure such that a calibration function, relating the cuff pressure to the arterial blood pressure (usually in the upper arm) is no longer valid and the blood pressure readings become inaccurate.

This effect can be seen in FIG. 1 which shows the results of an experiment with a commercially-available volume clamp system whereby the blood pressure of the user was measured by attaching the cuff to the index finger of the user's right hand. The y-axis of FIG. 1 shows the blood pressure recorded by the volume-clamp BP monitoring device over time. Vasoconstriction was induced (and thus a reduction of blood perfusion) by submerging the left hand in a bucket of cold water around time t=375 s. FIG. 1 shows that after submersion, the systolic blood pressure (SBP) is underestimated by about 13 mmHg and the diastolic blood pressure (DBP) by about 10 mmHg.

As a reference, an arm cuff was placed on the left arm, to measure the systolic and diastolic blood pressure by a standard oscillometric method. This showed that the systolic and diastolic blood pressure actually stayed approximately constant during the experiment. However, the volume clamp system shows a decrease in blood pressure just after submerging the hand in the cold water and continues to underestimate it from that time onwards. This can be explained by the fact that due to vasoconstriction, a PPG-signal increases, while the volume clamp method is based on keeping the PPG-signal constant. The control system therefore makes the PPG-signal equal to the value it had before the vasoconstriction by lowering the cuff pressure. This is interpreted by the volume clamp system as a decrease in blood pressure.

SUMMARY OF THE INVENTION

Existing volume-clamp BP monitoring devices are calibrated on initial use to determine the calibration function mentioned above. The monitoring devices are subsequently recalibrated since measurements of BP can drift over time due to various reasons. Recalibration of the BP monitoring device will address problems with accuracy in the BP measurements caused by changes in blood perfusion that have occurred since the last calibration.

However, as described above, blood perfusion can change considerably and lead to BP measurements from a volume-clamp BP monitoring device being erroneous, and these changes can occur frequently due to for example temperature-related vasoregulation and vaso-active medication. One solution to this problem is to recalibrate the BP monitoring device at regular intervals. However, during recalibration the BP monitoring device is not able to make blood pressure measurements (since a recalibration requires the cuff to be put through a range of pressures), so the number of recalibration events and the duration of recalibration should be as short as possible when continuous BP measurements are required. This means that the BP monitoring device should only calibrate when necessary and should keep the time per calibration as short as possible.

Current volume-clamp BP monitoring devices do not meet this aim as they use a fixed time interval or a predetermined number of heart beats between recalibration events. As a result, there may be a significant duration of time between a change in blood perfusion and the next scheduled recalibration which can lead to a series of inaccurate measurements being taken. Furthermore, the device may recalibrate unnecessarily, thereby wasting time when the device would otherwise be making accurate measurements.

Therefore there is a need for improvements to volume-clamp blood pressure monitoring devices to address these issues.

According to a first aspect, there is provided an apparatus for measuring the blood pressure, BP, of a user, the apparatus comprising a volume-clamp BP monitoring device that comprises a first pressure device for applying pressure to a first part of the body of the user, a first photoplethysmogram, PPG, sensor for obtaining a first PPG signal from the first part of the body of the user, and a control unit that is configured to analyse the first PPG signal and to control the pressure of the first pressure device to maintain the first PPG signal at a constant level and to determine the BP of the user from the pressure of the first pressure device; and a second sensor for measuring a physiological characteristic of the user in a second part of the body of the user; wherein the apparatus is configured to analyse the measured physiological characteristic to determine a measure of the blood perfusion in the second part of the body of the user, and to determine whether to perform a recalibration of the volume-clamp BP monitoring device on the basis of changes in the blood perfusion.

In preferred embodiments the volume-clamp BP monitoring device further comprises a second pressure device that is for applying pressure to the second part of the body of the user and the second sensor, wherein the second sensor is a second PPG sensor, and wherein the apparatus is configured to alternately measure the BP of the user using the first pressure device and the first PPG sensor, and the second pressure device and the second PPG sensor.

In preferred embodiments the apparatus is configured to analyse the PPG signal from the second PPG sensor to determine the measure of the blood perfusion in the second part of the body of the user when the first pressure device and first PPG sensor are being used to measure the BP of the user in the first part of the body of the user; and further configured to analyse the signal from the first PPG sensor in to determine the measure of the blood perfusion in the first part of the body of the user when the second pressure device and second PPG sensor are being used to measure the BP of the user in the second part of the body of the user.

In some embodiments the apparatus is further configured to use the second pressure device to apply pressure to the second PPG sensor to contact the second PPG sensor with the second part of the body of the user when the first pressure device and the first PPG sensor are being used to measure the BP of the user.

In some embodiments the apparatus is further configured to use the first pressure device to apply pressure to the first PPG sensor to contact the first PPG sensor with the first part of the body of the user when the second pressure device and the second PPG sensor are being used to measure the BP of the user.

In some embodiments the second sensor is a sensor that is placed in contact with the second part of the body of the user. In alternative embodiments the second sensor is a sensor that is not in contact with the second part of the body of the user.

In some embodiments the measure of blood perfusion is one or more of a DC value of the measured physiological characteristic, the amplitude of pulses in the measurements, and characteristics of the morphology of pulses in the measured physiological characteristic.

In some embodiments the measure of blood perfusion is a DC value of the measured physiological characteristic, and wherein the apparatus is configured to analyse the measured physiological characteristic to determine a DC value in the measurements, and to determine whether to perform a recalibration of the volume-clamp blood pressure monitoring device on the basis of changes in the determined DC value.

In some embodiments the measure of blood perfusion is the amplitude of pulses in the measurements, and wherein the apparatus is configured to analyse the measured physiological characteristic to determine the amplitude of pulses in the measurements, and to determine whether to perform a recalibration of the volume-clamp blood pressure monitoring device on the basis of changes in the amplitude of the pulses.

In some embodiments the measure of blood perfusion is a characteristic of the morphology of pulses in the measured physiological characteristic, and wherein the apparatus is configured to determine characteristics of the morphology of pulses in the measurements of the physiological characteristic, and to determine whether to perform a recalibration of the volume-clamp blood pressure monitoring device on the basis of changes in the characteristics.

In some embodiments the measure of blood perfusion is a combination of the DC value, AC value and/or one or more characteristics of the morphology of pulses of the measured physiological characteristic, and wherein the apparatus is configured to analyse the measured physiological characteristic to determine a DC value, an AC value and/or one or more characteristics of the morphology of pulses in the measurements, and to determine whether to perform a recalibration of the volume-clamp blood pressure monitoring device on the basis of changes in the determined DC value, AC value and/or one or more characteristics of the morphology of pulses.

In some embodiments the control unit is further configured to perform a recalibration of the volume-clamp BP monitoring device.

In some embodiments the control unit is configured to perform a recalibration by (i) applying a range of pressures to the first body part using the first pressure device and obtaining a PPG signal using the first PPG sensor at multiple pressures in the range of pressures; (ii) analysing the obtained PPG signals to select the constant level for the first PPG signal; and (iii) determining a calibration function that relates the pressure of the first pressure device to the BP of the user.

In some embodiments the range of pressures comprises pressures above and below a pressure of the first pressure device previously required to maintain the first PPG signal at the constant level.

In some embodiments the range of pressures comprises pressures above a pressure of the first pressure device previously required to maintain the first PPG signal at the constant level in the event that the blood perfusion has decreased.

In some embodiments the range of pressures comprises pressures below a pressure of the first pressure device previously required to maintain the first PPG signal at the constant level in the event that the blood perfusion has increased.

In some embodiments the minimum and/or maximum of the range of pressures are determined based on the magnitude of the change in blood perfusion.

In some embodiments the control unit is configured to perform a recalibration by recalculating or scaling the constant level for the first PPG signal or recalculating or scaling one or more calibration constants in a calibration function that relates the pressure of the first pressure device to the BP of the user, wherein the recalculation or rescaling is based on the magnitude of the change in blood perfusion.

In some embodiments the first part of the body is a finger. In some embodiments the second part of the body is another finger.

According to a second aspect, there is provided a method of measuring the blood pressure, BP, of a user, the method comprising measuring the blood pressure of the user using a volume-clamp BP monitoring device that comprises a first pressure device for applying pressure to a first part of the body of the user, a first photoplethysmogram, PPG, sensor for obtaining a first PPG signal from the first part of the body of the user, and a control unit for analysing the first PPG signal and controlling the pressure of the first pressure device to maintain the first PPG signal at a constant level over time and determining the BP of the user from the pressure of the first pressure device; measuring a physiological characteristic of the user in a second part of the body of the user; analysing the measured physiological characteristic to determine a measure of the blood perfusion in the second part of the body of the user; and determining whether to perform a recalibration of the volume-clamp BP monitoring device on the basis of changes in the blood perfusion.

In preferred embodiments the volume-clamp BP monitoring device further comprises a second pressure device for applying pressure to the second part of the body of the user and the second sensor, wherein the second sensor is a second PPG sensor, and wherein the method further comprises alternately measuring the BP of the user using the first pressure device and the first PPG sensor, and the second pressure device and the second PPG sensor.

In preferred embodiments the step of analysing comprises analysing the PPG signal from the second PPG sensor to determine the measure of the blood perfusion in the second part of the body of the user when the first pressure device and first PPG sensor are being used to measure the BP of the user in the first part of the body of the user; and analysing the signal from the first PPG sensor in to determine the measure of the blood perfusion in the first part of the body of the user when the second pressure device and second PPG sensor are being used to measure the BP of the user in the second part of the body of the user.

In some embodiments the method further comprises the step of using the second pressure device to apply pressure to the second PPG sensor to contact the second PPG sensor with the second part of the body of the user when the first pressure device and the first PPG sensor are being used to measure the BP of the user.

In some embodiments the method further comprises the step of using the first pressure device to apply pressure to the first PPG sensor to contact the first PPG sensor with the first part of the body of the user when the second pressure device and the second PPG sensor are being used to measure the BP of the user.

In some embodiments the second sensor is a sensor that is placed in contact with the second part of the body of the user. In alternative embodiments the second sensor is a sensor that is not in contact with the second part of the body of the user.

In some embodiments the measure of blood perfusion is one or more of a DC value of the measured physiological characteristic, the amplitude of pulses in the measurements, and characteristics of the morphology of pulses in the measured physiological characteristic.

In some embodiments the measure of blood perfusion is a DC value of the measured physiological characteristic, and wherein the step of analysing comprises analysing the measured physiological characteristic to determine a DC value in the measurements, and the step of determining comprises determining whether to perform a recalibration of the volume-clamp blood pressure monitoring device on the basis of changes in the determined DC value.

In some embodiments the measure of blood perfusion is the amplitude of pulses in the measurements, and wherein the step of analysing comprises analysing the measured physiological characteristic to determine the amplitude of pulses in the measurements, and the step of determining comprises determining whether to perform a recalibration of the volume-clamp blood pressure monitoring device on the basis of changes in the amplitude of the pulses.

In some embodiments the measure of blood perfusion is a characteristic of the morphology of pulses in the measured physiological characteristic, and wherein the step of analysing comprises determining characteristics of the morphology of pulses in the measurements of the physiological characteristic, and the step of determining comprises determining whether to perform a recalibration of the volume-clamp blood pressure monitoring device on the basis of changes in the characteristics.

In some embodiments the method further comprises the step of performing a recalibration of the volume-clamp BP monitoring device.

In some embodiments the step of performing a recalibration comprises performing a recalibration by (i) applying a range of pressures to the first body part using the first pressure device and obtaining a PPG signal using the first PPG sensor at multiple pressures in the range of pressures; (ii) analysing the obtained PPG signals to select the constant level for the first PPG signal; and (iii) determining a calibration function that relates the pressure of the first pressure device to the BP of the user.

In some embodiments the range of pressures comprises pressures above and below a pressure of the first pressure device previously required to maintain the first PPG signal at the constant level.

In some embodiments the range of pressures comprises pressures above a pressure of the first pressure device previously required to maintain the first PPG signal at the constant level in the event that the blood perfusion has decreased.

In some embodiments the range of pressures comprises pressures below a pressure of the first pressure device previously required to maintain the first PPG signal at the constant level in the event that the blood perfusion has increased.

In some embodiments the minimum and/or maximum of the range of pressures are determined based on the magnitude of the change in blood perfusion.

In some embodiments the step of performing a recalibration comprises performing by recalculating or scaling the constant level for the first PPG signal or recalculating or scaling one or more calibration constants in a calibration function that relates the pressure of the first pressure device to the BP of the user, wherein the recalculation or rescaling is based on the magnitude of the change in blood perfusion.

In some embodiments the first part of the body is a finger. In some embodiments the second part of the body is another finger.

According to a third aspect, there is provided a computer program product comprising a computer readable medium having computer readable code embodied therein, the computer readable code being configured such that, on execution by a suitable computer or processor, the computer or processor is caused to perform any of the methods described above.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 2:
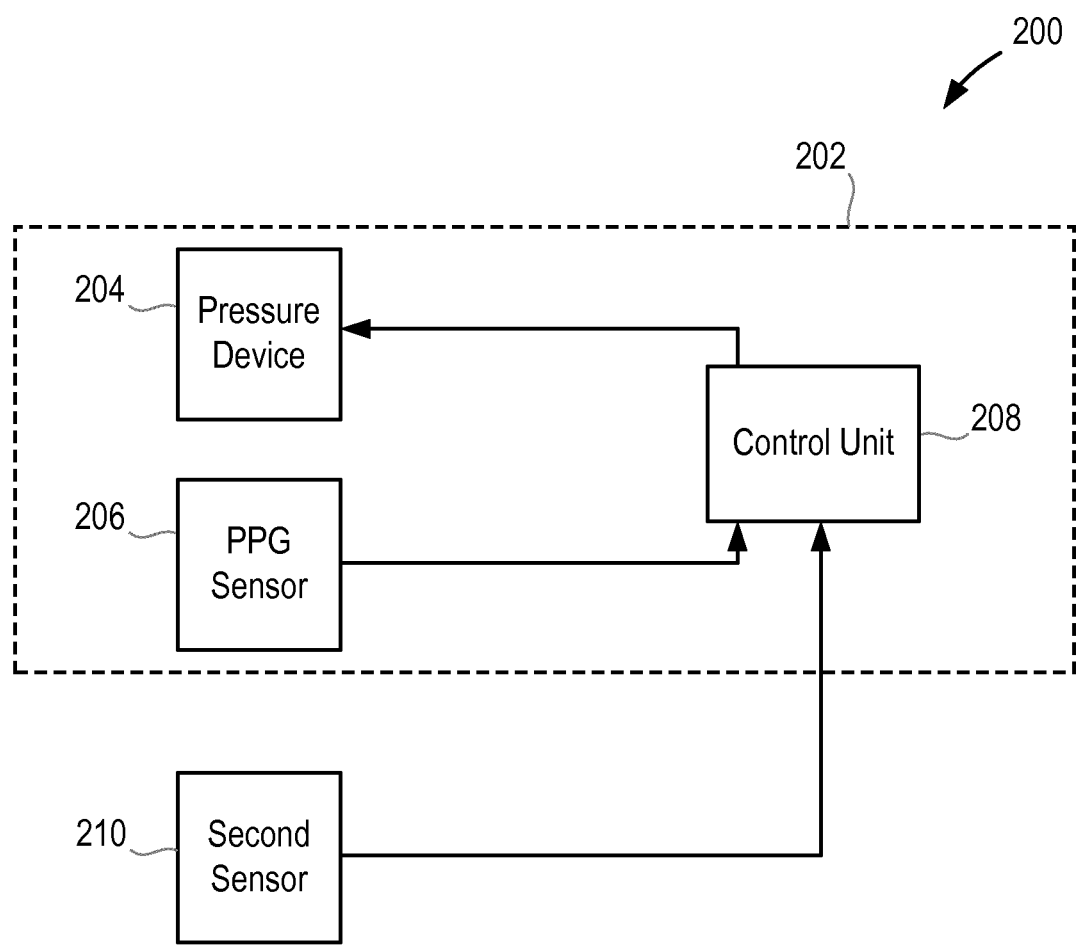
FIG. 2 shows an example apparatus according to an embodiment.

FIG. 2 shows an apparatus 200 for measuring the blood pressure (BP) of a user according to an embodiment. The apparatus comprises a volume-clamp BP monitoring device 202 for measuring the BP of the user. The volume-clamp BP monitoring device comprises a first pressure device 204 for applying pressure to a first part of the body of the user, a first photoplethysmogram, PPG, sensor 206, held against the skin by the first pressure device 204, for obtaining a first PPG signal from the first part of the body of the user, and a control unit 208 that is configured to analyse the first PPG signal, control the pressure of the first pressure device 204 and determine the BP of the user.

The control unit 208 is configured to adjust the pressure of the first pressure device 204 to maintain the first PPG signal at a constant level (known as a setpoint or setpoint level). The control unit 208 determines the blood pressure of the user from the pressure of the first pressure device 204 and a calibration function that is determined during a calibration procedure. The calibration procedure is described in more detail below.

Unless otherwise indicated below, the volume-clamp BP monitoring device 202 measures the BP of the user in a conventional manner.

In some embodiments, the first pressure device 204 may comprise a pump and an inflatable cuff designed to be placed around a body part of a user. The cuff may be inflated to exert pressure on the body part using the pump under control of the control unit 208. Those skilled in the art will appreciate that the first pressure device 204 may take other forms than an inflatable cuff. Preferably the first pressure device 204 is configured to be worn on the user's finger, but in other embodiments the first pressure device 204 is configured to be worn on another body part, such as the user's arm, leg or a toe. In other embodiments, the first pressure device 204 may comprise a pump that pumps a constant flow and a multistate valve that controls the pressure increase of an inflatable cuff.

The PPG sensor 206 is generally conventional and comprises a light source for emitting light towards a body part (e.g. a finger) and a light sensor for detecting light that has transmitted through or reflected from the body part. The PPG sensor 206 outputs a PPG signal to the control unit 208. Those skilled in the art will be aware of suitable types of PPG sensors that can be used in volume-clamp BP monitoring devices. In some embodiments, the wavelength of the light emitted by the PPG sensor 206 is at the isosbestic wavelength of oxyhemoglobin and reduced haemoglobin (±800 nm). At this wavelength the PPG signal is not affected by changes in blood oxygenation.

The control unit 208 may comprise processing circuitry for controlling the pressure of the first pressure device 204 and processing the signal from the PPG sensor 206. The control unit 208 may also comprise a memory module for storing computer readable code to enable the processing circuitry to perform the method according to the invention, and any other information required for or during the operation of the volume-clamp BP monitoring device 202.

Figure 1:
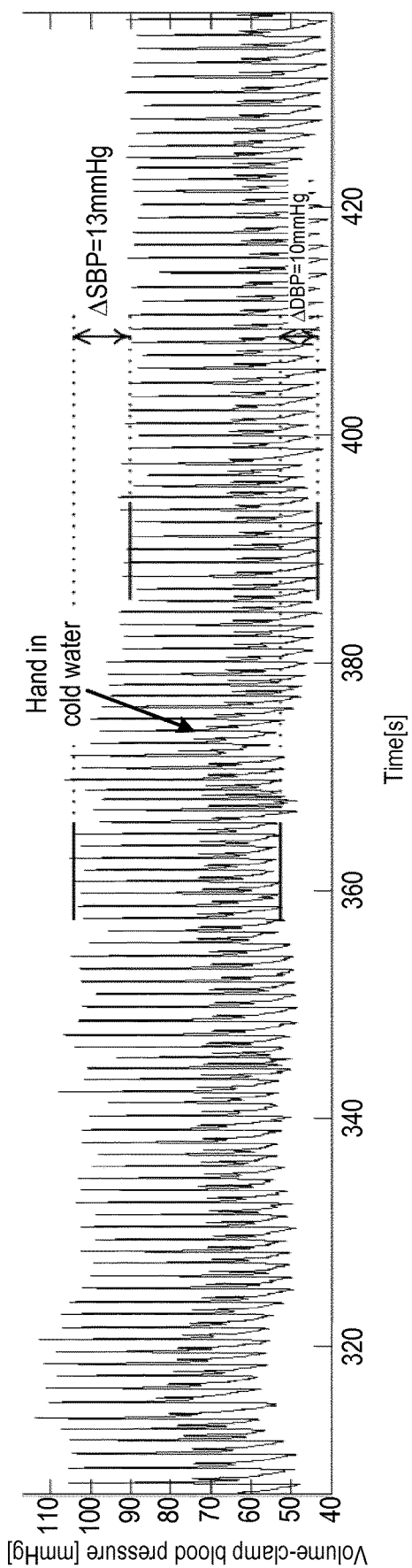
FIG. 1 is a graph showing blood pressure readings of a user over time.

As described above, the control unit 208 determines the blood pressure of the user from the pressure of the first pressure device 204 and a calibration function that is determined during a calibration procedure. However, FIG. 1 illustrates that errors will be introduced to the BP measurements from the volume-clamp BP monitoring device 202 when there are changes in the blood perfusion.

Conventionally, the control unit 208 may be configured to perform a recalibration of the volume-clamp BP monitoring device 202 to determine a new or updated calibration function after a certain time interval or after a certain number of heart beats. However, this means that a recalibration may be performed unnecessarily, or not quickly enough after a change in perfusion has occurred.

Therefore, the invention provides that blood perfusion is monitored, and a recalibration triggered or initiated in response to detecting a change or significant change in the blood perfusion.

Thus, in accordance with the invention, in addition to the volume-clamp BP monitoring device 202, the apparatus 200 comprises a second sensor 210 that measures a physiological characteristic from a second part of the body of the user, and the apparatus 200 is configured to analyse the measured physiological characteristic to determine a measure of blood perfusion of the user, and to determine whether to perform a recalibration of the volume-clamp blood pressure monitoring device 202 on the basis of changes in the blood perfusion. The second sensor 210 can be any type of sensor whose measurements can be processed to determine a measure of blood perfusion. The second sensor 210 is a separate sensor to the first sensor 206, (i.e. it is a different sensor to the first sensor 206). The second part of the body is different (separate) to the part of the body that the first sensor 206 measures the PPG signal from. Preferably the second sensor 210 is a sensor that obtains a PPG signal for the second part of the body of the user.

To avoid any influence on the measured physiological characteristic from the pressure exerted on the first part of the body by the first pressure device 204, the second part of the body is preferably physically separated from and non-overlapping with the area of the user's skin that is in contact with first pressure device 204 or that is affected by the first pressure device 204. Where the first part of the body is a finger, the second part of the body may be another finger on the same hand, a finger on the opposite hand, or a different part of the body of the user, such as an arm, leg, ear or toe. Where the first part of the body is not a finger, the second sensor 210 may be located on a finger or another part of the body such as an arm, leg, ear or toe.

In some embodiments the second sensor 210 is a sensor that is placed in physical contact with the user's body. For example, the second sensor 210 can be a second PPG sensor in contact with the skin. This PPG sensor may measure the amount of light at one or more wavelengths. In one embodiment, the PPG sensor can also be used to measure the oxygenation of the blood. Such sensors are often used in the hospital and are referred to as SpO2 (pulse oximeter) sensors. Other contact sensors that can be used for physiological measurements that are related to perfusion are for example laser-speckle, laser-Doppler or skin temperature sensors. Note that skin temperature and blood perfusion are correlated; and increase in blood perfusion will usually increase the skin temperature.

Alternatively, the second sensor can be a sensor that is located remotely from the user and does not make physical contact with the user's skin. In this case, the second sensor 210 can be a camera, video recorder or other imaging device and the control unit 208 can determine the blood perfusion from the recorded image data. In one embodiment, the captured images are used as a source for a PPG measurement in which the changes in the amount of blood are measured by the amount of ambient light that is reflected back from the skin towards the camera (this is also known as remote PPG, rPPG). In another embodiment, the captured images are used to get information on temperature, using the principle of a thermal camera, which is based on infrared light irradiated from the body. In yet another embodiment, a laser is used to illuminate the body and the captured images are analysed with laser-speckle analysis. Laser Doppler is another example of a technique that can be used in non-contact mode.

A person skilled in the art will be aware of other types of sensors for measuring the perfusion. The perfusion measurement could also be performed by using a combination of sensors. For example, to get a measure for perfusion, the signals of both a contact PPG sensor and a thermal camera could be used.

In some embodiments, the second sensor 210 can be connected to the control unit 208 and the control unit 208 can process the signals from the second sensor 210 to determine the measure of the blood perfusion. In alternative embodiments, the apparatus 200 may comprise a further control unit or other processing circuitry that is configured to process the signals from the second sensor 210 to determine the measure of the blood perfusion and to provide the measure of the blood perfusion to the control unit 208. In further alternative embodiments, the apparatus 200 may comprise a further control unit or other processing circuitry that is configured to process the signals from the second sensor 210 to determine the measure of the blood perfusion and to determine whether a recalibration of the volume-clamp BP monitoring device 202 should be triggered. In that embodiment, the further control unit or other processing circuitry can be configured to send a signal to the control unit 208 to trigger the recalibration of the volume-clamp BP monitoring device 202.

It will be appreciated that FIG. 2 only shows the components required to illustrate this aspect of the invention, and in a practical implementation the apparatus 200 may comprise additional components to those shown. For example, apparatus 200 may additionally comprise components such as a communication module for enabling the BP measurements to be communicated to a remote computer, one or more user interface components that allow a user (e.g. the wearer of the first pressure device 204 or healthcare professional) to interact with and control the BP monitoring device, and/or a battery or other power supply for powering the apparatus 200.

Figure 3:
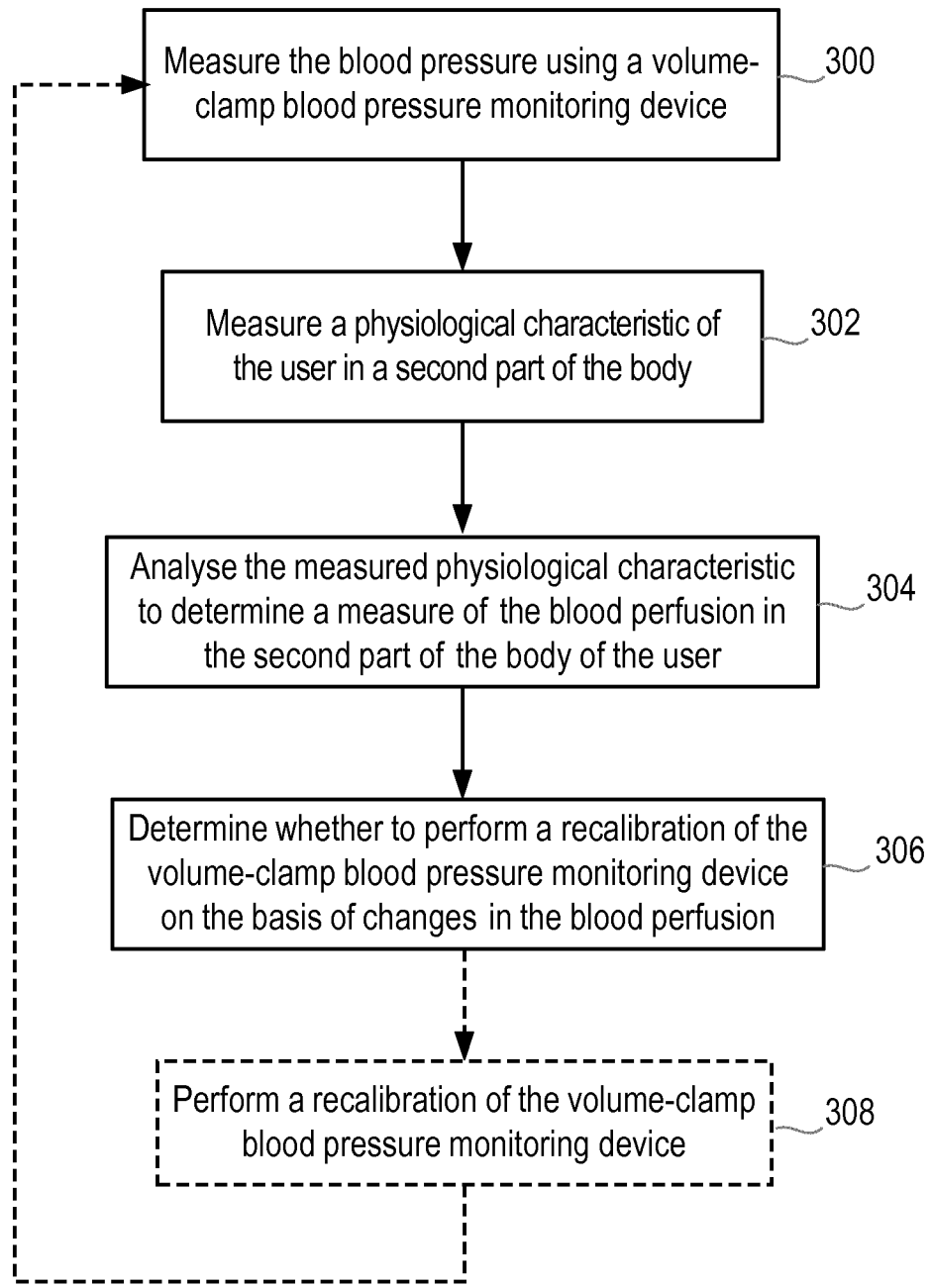
FIG. 3 shows an example method according to an embodiment.

FIG. 3 shows a method of measuring the blood pressure in a body part of a user according to the invention using an apparatus as shown in FIG. 2. The method comprises the step of measuring the blood pressure of the user using the volume-clamp blood pressure monitoring device 202 (step 300).

The method further comprises the step of measuring a physiological characteristic of the user in a second part of the body of the user (step 302). As noted above, the physiological characteristic is measured using a second sensor 210, for example a PPG sensor. Also as noted above the second sensor 210 is separate from the sensor in the volume-clamp blood pressure monitoring device 202, and the second part of the body is separate from the part of the body that the first sensor 206 measures the PPG signal from (e.g. in some embodiments the first and second body parts are different fingers on the same hand). In step 304 the measured physiological characteristic is analysed to determine a measure of the blood perfusion in the second part of the body of the user.

Measurements of the blood perfusion obtained over time are analysed to determine changes in the blood perfusion, and it is determined whether a recalibration of the volume-clamp blood pressure monitoring device 202 should be performed on the basis of changes in the measured blood perfusion (step 306).

In the event that a recalibration is to be performed, the method further comprises the step of recalibrating the volume-clamp blood pressure monitoring device (step 308). On completion of the recalibration, the method returns to step 300 and starts to measure the BP of the user. Techniques for calibrating and recalibrating the monitoring device 202 are described in more detail below.

It will be appreciated that as a volume-clamp BP monitoring device 202 can be used to continuously measure the BP of the user, steps 302, 304 and 306 will typically be performed while the BP monitoring device is measuring the BP according to step 300. The order of the steps shown in FIG. 3 should therefore not be considered limiting.

As noted above, in terms of the measurement of blood pressure, the volume-clamp BP monitoring device 202 is generally conventional, and thus step 300 comprises operating the volume-clamp BP monitoring device 202 to measure BP in a generally conventional manner. Thus, in step 300, an inflatable cuff or other pressure device that is placed around a body part such as a finger is inflated to a particular pressure in order to exert pressure on the arteries in that body part. A signal from a PPG sensor that is attached to the cuff is analysed. The intensity of the PPG signal depends on the diameter of the arteries in the body part, which in turn depends on the amount of blood in the arteries and the blood pressure. Using the PPG sensor and cuff, the blood pressure can be measured using a closed-loop control system whereby changes in the PPG signal are used to trigger a change in the pressure applied by the cuff so that the arteries are kept at a constant diameter (and thus the PPG signal is kept at a constant value). As such, when the pressure in the arteries (and thus the diameter of the arteries) increases or decreases, the pressure in the cuff is increased or decreased to compensate. A calibration function is used to relate the pressure of the first pressure device 204 to a BP measurement for the user.

Figure 4:
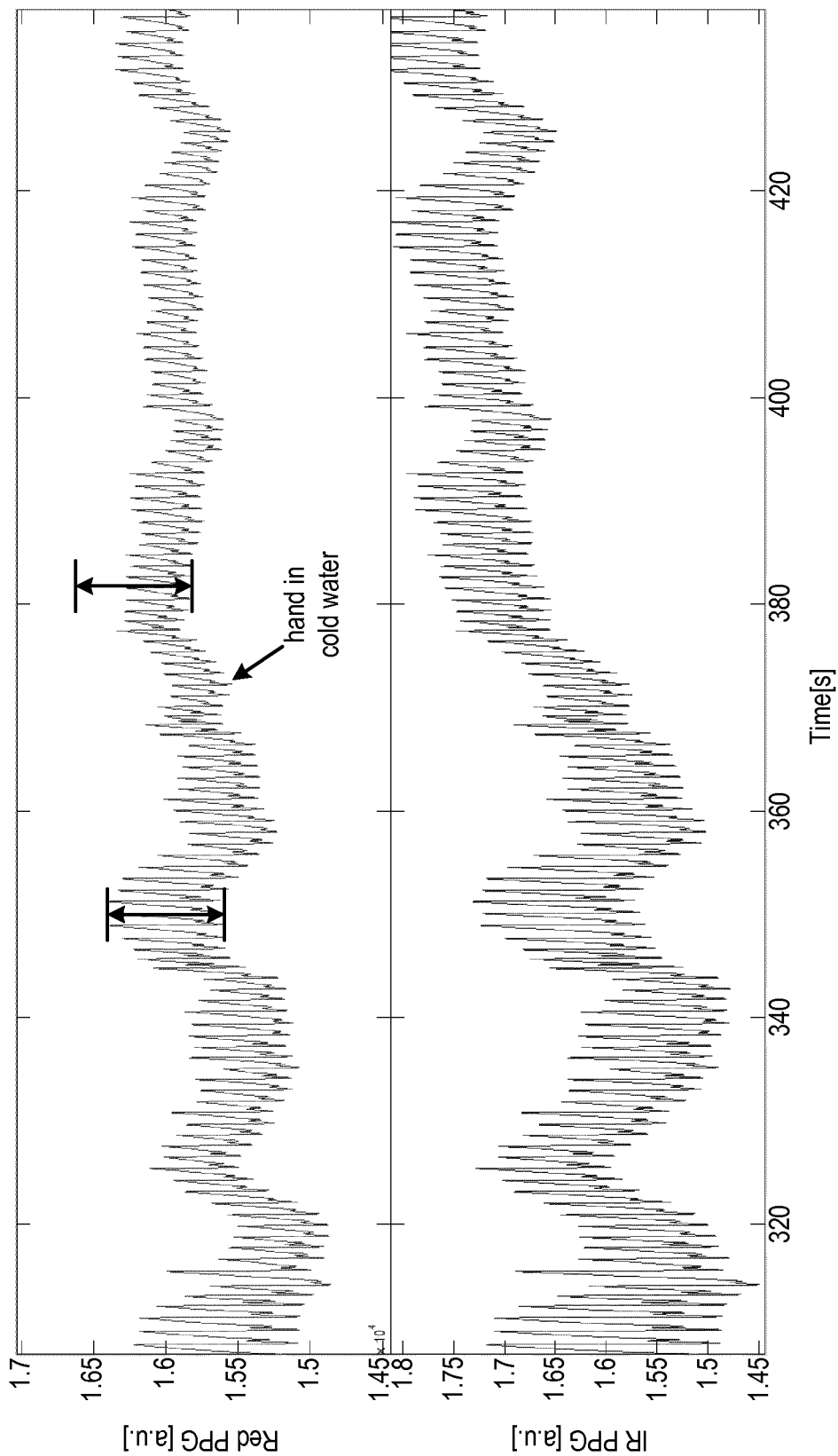
FIG. 4 is a graph showing PPG measurements of a user over time.

As noted above, in preferred embodiments the second sensor is a PPG sensor or other type of sensor that provides a PPG signal for the second body part. FIG. 4 shows PPG signals from the same experiment that was used to provide the graph of FIG. 1, with the PPG signals being obtained from a PPG sensor on the middle finger of the right hand (with the cuff of the volume-clamp BP monitoring device being attached to the index finger of the right hand). FIG. 4 shows two PPG signals, one obtained using a red light source (the upper graph), and the other using an infrared light source (the lower graph). In both graphs the left hand of the user is submerged in cold water at approximately t=375 s, thereby causing vasoconstriction and thus a lower blood perfusion.

As is known, a PPG sensor measures the amount of light that is reflected back from or transmitted through a body part (for example a fingertip). When the perfusion level drops, the extremities such as the fingers and toes contain less blood and therefore absorb less light from the PPG, leading to a higher signal on the photo detector (light sensor) of the PPG sensor and thus to a higher overall PPG signal, which can be seen in FIG. 4 (and is most pronounced in the lower graph of FIG. 4). The overall PPG signal level is referred to herein as a low frequency component or DC value, and this DC value fluctuates on timescales greater than the time between heart beats. The amplitude of the high frequency components of the PPG signal, which are referred to herein as AC values, are caused by the pulsations of the heart. The vertical arrows in the upper graph of FIG. 4 have the same length and show that the pulse amplitude decreases when the left hand is put in cold water and the blood perfusion decreases.

Furthermore, when the perfusion lowers, the micro vessels constrict and the reflected pressure wave changes which results in an altered morphology of the pulses in the signal. This can be seen in FIG. 5.

Figure 5:
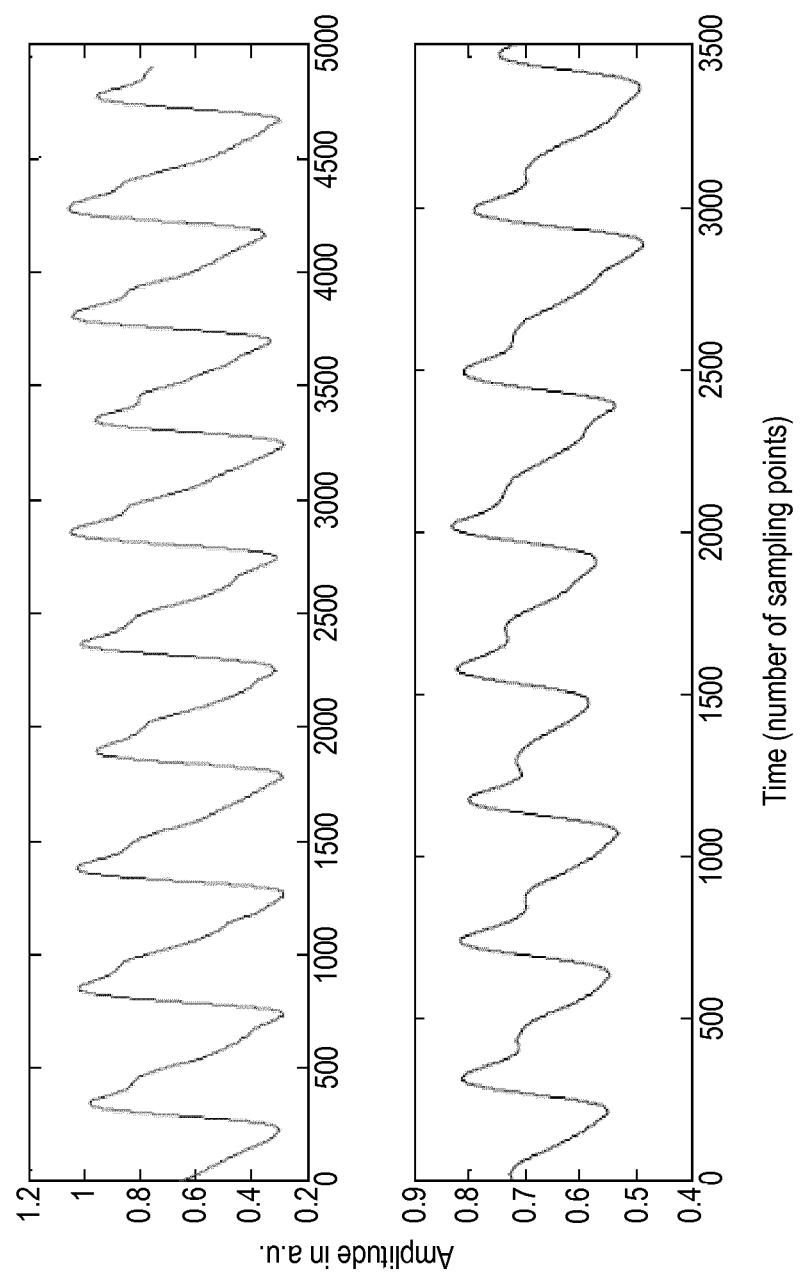
FIG. 5 shows the shape of the PPG sensor readings before and after a change in perfusion in more detail.

FIG. 5 shows pulses in more detail and in particular shows an inverted PPG signal before (top graph) and after (lower graph) cold exposure as a function of time. This Figure was taken from Chapter 4 ("Investigations on the effect of local cold exposure on the photoplethysmographic signals") in thesis "Selected cardiovascular studies based on photoplethysmography technique", V. K. Jayasree, International School of Photonics, Cochin University of Science and Technology, India, 2009. It shows the effect of cold exposure, leading to a decrease in perfusion, on pulse morphology (i.e. the shape of the pulses). In particular the chapter in the aforementioned thesis investigated the effect on pulse-morphology features with the names "dicrotic notch", "normalized pulse width", "skin vasomotor reflex", "area index", "half width amplitude" and "latency between systolic and diastolic peak". The definitions of these features are given in the chapter. It is noted that by cold exposure (and thus decrease in perfusion), the dicrotic notch becomes sharper and the normalized pulse width, skin vasomotor reflex, area index, half width amplitude and latency between systolic and diastolic peaks decrease.

Thus, FIGS. 4 and 5 demonstrate that when blood perfusion decreases, the DC value of the PPG signal increases, the amplitudes of the pulses decrease and their morphology changes. In the case that there is an increase in perfusion by vasodilatation (e.g. if the hand were removed from the cold water bucket and put into warm water), the DC value, AC amplitude and wave morphology characteristics would change in the reverse direction to that listed above, i.e. the amplitude would increase, the DC value would decrease, the dicrotic notch would become less pronounced and the normalized pulse width, skin vasomotor reflex, area index, half width amplitude and latency between systolic and diastolic peaks would increase.

A measure for perfusion can be determined from one or more of the above mentioned features in the PPG signal. However, determining a measure for perfusion from a PPG signal is not limited to the above-mentioned features but could also include other features, such as full width at half maximum and maximum upward slope.

A measure of the blood perfusion in the user can therefore be determined in step 304 by analysing the PPG-signal of a PPG sensor under constant contact pressure (i.e. the sensor and the part of the body that it is measuring is not subject to varying pressure); especially the pulse amplitude, pulse morphology and/or DC value of the signal, and these measures can be observed over time to determine changes in the blood perfusion for use in step 306.

The 'DC' value of a PPG signal can be obtained in several ways. In some embodiments, the PPG signal can be low pass filtered. A suitable cut-off frequency for the low pass filter can be a frequency that is below the heart rate, e.g. 0.2 Hz. In alternative embodiments, a moving average of the PPG signal can be calculated over a several-second window. Those skilled in the art will be aware of other ways in which a low frequency or DC value of a PPG signal can be determined.

In some embodiments, the amplitude of the PPG signal can be obtained by determining the per-beat maximum and minimum of the signal across a heartbeat and subtracting the minimum from the maximum. Those skilled in the art will be aware of other ways in which the amplitude of a PPG signal can be determined.

In some embodiments, one or more characteristics of the morphology of the pulse can be determined. In some embodiments the characteristics can include any one or more of the normalized pulse width, skin vasomotor reflex, area index, half width amplitude and latency between systolic and/or diastolic peaks in the signal.

The normalized pulse width (NPW) is given by:

$$NPW=PW/CP \qquad (1)$$

where PW is the peak width and CP is the cardiac period. PW is the width of a PPG pulse at a predetermined amount (e.g. 10%) of the pulse height (PH—which is the difference between the maximum of a cardiac cycle and the previous minimum), and CP is the time between the peaks of two consecutive cardiac cycles.

The skin vasomotor reflex (SVMR) ratio is given by:

$$SVMR \text{ ratio}=[(BL-MV)/BL]*100 \qquad (2)$$

where BL is the baseline value (the maximum amplitude of the peak) and MV is the minimal value (the minimum value of the amplitude).

The area index is based on the variation in a ratio of the area under the systolic peak in the PPG signal to the area of the remaining portion of the cardiac cycle. The area index (AR) is given by:

$$AR=(A_1-A_2)/A_2 \qquad (3)$$

where $A_1$ is the area under the PPG signal from the start of the cardiac cycle (e.g. given by the minimum amplitude) to the systolic peak (the peak amplitude) and $A_2$ is the area under the PPG signal from the systolic peak to the end of the cardiac cycle. Those skilled in the art will be aware of various techniques for determining $A_1$ and $A_2$.

The half width amplitude (HWA) is defined as the width of the PPG pulse at half of the peak amplitude. Those skilled in the art will be aware of various techniques for determining the HWA.

A PPG signal has a peak (the systolic peak) and a later peak or point of inflection that occurs a short time ($\Delta T$) after the systolic peak in early diastole. This $\Delta T$ is the latency between systolic and/or diastolic peaks in the signal.

Since the PPG signal parameters described above can be influenced by factors other than blood perfusion, such as motion (including respiratory motion), in some embodiments the reliability of the measure of perfusion, or the reliability of the measure of the change in the blood perfusion are improved by using a combination of the PPG signal parameters. Thus, in some embodiments, step 304 can comprise determining two or more different parameters from the PPG signal and combining the two or more parameters to determine the measure of the blood perfusion. The combination can be a linear combination or a non-linear combination such as the PPG amplitude divided by the DC value. In further or alternative embodiments, the reliability can be improved by averaging the parameter or parameters over a number of heart beats (e.g. 5). However, since a PPG signal is known to vary with respiration rate, it is preferable to take the average over a sufficient number of beats to cover two or more respiration cycles.

As described above, having determined the measure of the blood perfusion and the change in blood perfusion over time, step 306 comprises determining whether to perform a recalibration based on the change in perfusion. In some embodiments, a recalibration can be triggered when there is a substantial change in blood perfusion. In some embodiments a substantial change can correspond to a change of at least 10% in the blood perfusion (i.e. at least a 10% change in the measure of the blood perfusion) from the blood perfusion when the monitoring device 202 was last calibrated or recalibrated. In other embodiments a substantial change can correspond to a change of at least 20%, or some other suitable percentage value.

In some embodiments, a substantial change in blood perfusion can be identified by comparing the measured blood perfusion change to a threshold. The threshold may be an absolute value that is the same for each user or for a population of users, such as users of the same age or gender. Alternatively, the threshold may be user specific and calculated for each user based on their particular characteristics.

In some embodiments, a substantial change in blood perfusion can be identified by comparing the perfusion measure with a long term trend of the perfusion measure and using a certain ratio as the trigger for recalibration. In some embodiments, the trend measure can be obtained by calculating a moving average of the blood perfusion measure over a time window (e.g. 1 minute) and determining whether to perform a recalibration based on a comparison with the current perfusion measure. For example, if the current perfusion measure is below or above a certain ratio, then there is a substantial change in blood perfusion and recalibration should be initiated. For instance, if PerfusionCurrent (the current perfusion measure)<0.9×PerfusionTrend (the moving average), then recalibration should be initiated.

Those skilled in the art will be aware of other ways in which a substantial change in blood perfusion can be determined from the measure of blood perfusion.

In some embodiments, when a recalibration is triggered in response to detecting a substantial change in blood perfusion, the calibration/recalibration can be performed in a conventional manner. That is, the recalibration can comprise performing a full calibration of the monitoring device 202 as described below.

Calibration of the sensor values to real blood pressure readings consists of three steps. In the first step, the unstressed volume of the artery has to be found, i.e. the DC setpoint value of the light intensity has to be determined. In the second step, the pressure waveform in the cuff (or other pressure device) has to be translated into a blood pressure waveform. In the third step, the blood pressure waveform has to be translated into a blood pressure waveform that is relevant to a user.

The unstressed volume (the setpoint light intensity) can be determined as follows. During a calibration or recalibration procedure, a range of pressures is applied by the first pressure device 204, usually in a stepwise manner, while the response of the PPG signal of PPG sensor 206 is evaluated. This enables the selection of the light level measured by the PPG sensor 206 that, during the blood pressure measurements (after the (re)calibration procedure is completed), is to be kept constant by changing the pressure of the first pressure device 204. The determination of the setpoint generally relies on the resulting amplitude and/or waveform of a pulse in the PPG signal. Examples of how this setpoint can be chosen are given in "Physiocal, calibrating finger vascular physiology for Finapres", K. H. Wesseling et al. Homeostasis 1995; 36:67-82. For example, one method of setpoint selection is using the light intensity where the PPG amplitude at constant external pressure is maximal. When the setpoint has been determined, the pressure device 204 is used to keep the light intensity at the desired setpoint level.

The second step is to relate the pressure p of the first pressure device 204 to the blood pressure $BP_{device\_location}$ of the artery to which the external pressure is applied. The function that tries to resemble this relationship is referred to as $f_{p2BP}$. In its extensive form, $f_{p2Bp}$ depends on parameters like elasticity of the tissue between the first pressure device 204 and the artery, the cuff compliance (in case a cuff is used as the first pressure device), the light level of the setpoint and the method by which the setpoint is derived. The relationship between $BP_{device\_location}$ and p can thus be written as:

$$BP_{device\_location} = f_{p2BP}(p, \text{setpoint}, \text{cuff\_compliance}, \text{tissue\_elasticity}, \ldots) \quad (4)$$

The influence of cuff compliance and tissue elasticity might be neglected or determined only once. Therefore, in its simplest form, $f_{p2BP} = p$.

In the third step, the blood pressure at the location of interest, $BP_{final\_location}$, needs to be derived from $BP_{device\_location}$. In the most straightforward example, where a finger cuff is used as first pressure device 204, $BP_{device\_location}$ is the blood pressure in the finger artery, while $BP_{final\_location}$ is the blood pressure in the brachial artery in the upper arm. The brachial artery in the upper arm is most likely because clinicians are familiar with its blood pressure values, as often blood pressure measurements are determined at the upper arm. The transfer function, $f_{transfer}$, links $BP_{device\_location}$ with $BP_{final\_location}$. It might be an empirically determined function, which can take into account the user's age and gender, and possibly weight or other parameters. The relationship between $BP_{device\_location}$ and $BP_{final\_location}$ can then be written as:

$$BP_{final\_location} = f_{transfer}(BP_{device\_location}, \text{age}, \text{gender}, \ldots) \quad (5)$$

The transfer function might also be a user-specific function, determined with an additional blood pressure measurement at the location of interest (e.g. with an arm cuff). The blood pressure waveform at the device location is then scaled such that its maximum coincides with the systolic value of the additional measurement, and the minimum coincides with the diastolic value of the additional measurement. Therefore, $f_{transfer}$ might be written as $$f_{transfer} = a*BP_{device\_location} + b \quad (6)$$

where a and b are calibration constants.

Another possibility is that the location of interest is the measurement location, for example if the volume-clamp measurement is done at the finger and the clinician is interested in the blood pressure of the finger artery, or if the volume-clamp method is performed on the upper arm. In those cases $f_{transfer}$ equals 1.

Substituting equation (4) in equation (5) gives the relationship between the pressure p of the first pressure device 204 and the blood pressure $BP_{final\_location}$ at the location of interest:

$$BP_{final\_location} = f_{transfer}(f_{p2BP}(p, \text{setpoint}, \ldots), \ldots) \quad (7)$$

This relationship is referred to as the calibration function. Note that, although described above as a three-step procedure, step two (determining the relationship between $BP_{device\_location}$ and p) and step three (determining the relationship between $BP_{final\_location}$ and $BP_{device\_location}$) can be merged, so without performing an intermediate calculation of $BP_{device\_location}$.

In alternative embodiments, when a recalibration is triggered in response to detecting a substantial change in blood perfusion, rather than perform a full calibration/recalibration procedure as described above, information about the change in perfusion can be used to minimise the recalibration time. In particular, the 'direction' in which perfusion has changed (i.e. increased or decreased), indicates the 'direction' in which recalibration should take place, and in some embodiments this information can be used to shorten the time taken to complete the first step of the recalibration procedure by limiting the range of pressures that need to be applied in order to determine the setpoint. In other words, the large range of pressures that is usually applied in the first step of a full calibration procedure can be reduced by using information about the change in perfusion.

For example, when blood perfusion has decreased and prior to any recalibration being performed, the pressure of the pressure device 204 that is measuring the blood pressure is lowered in order to keep the PPG signal of the sensor 206 inside that pressure device constant. If a recalibration is triggered as a result of the decrease in perfusion, then it is already known that the current pressure of the pressure device 204 is too low and that the pressure of the pressure device 204 should be increased during the recalibration.

Therefore, the time taken to complete the recalibration can be reduced, since there is no need to work through lower pressures than the current pressure of the pressure device 204 during the recalibration.

For an increase in perfusion, the opposite applies. Thus, when there is an increase in blood perfusion, the pressure of the pressure device 204 will be increased to keep the PPG signal constant, and so the recalibration will need to decrease the pressure of the pressure device 204. Pressures higher than the current pressure of the pressure device 204 can therefore be excluded from the range of pressures evaluated during the recalibration.

In further or alternative embodiments, the magnitude of the change in the perfusion can be used to reduce (or further reduce) the range of pressures evaluated during the recalibration. For example where there is a large change in perfusion, it may only be necessary to consider pressures that are different by more than a certain amount to the current pressure during the recalibration. Likewise where there is a small change in perfusion (but sufficient to trigger the recalibration), it may only be necessary to consider pressures that are within a certain amount or range of the current pressure.

In alternative embodiments, when a recalibration is triggered as a result of a change in blood perfusion, rather than perform a recalibration in which the pressure device 204 is put through a range or limited range of pressures in a first step, the first step can be skipped and the recalibration in step 308 can comprise recalculating or scaling one or more calibration constants in the calibration function or the setpoint based on the measured change in perfusion. This has the advantage that a quick recalibration can be performed, without having to cycle through a range of pressures in the full calibration procedure. In some embodiments this 'recalculation' can comprise changing the value of the amount of light (the setpoint) that is supposed to be detected by the first PPG sensor 206 in the pressure device 204 that is being used for the blood pressure measurement.

For example, suppose that an increase of blood perfusion with a percentage x is measured in step 304 and this change triggers a recalibration. The increase in perfusion will result in the amount of light that is detected by the PPG sensor 206 in the pressure device 204 being reduced with a factor y (which is related to the amount of the increase in perfusion). As the volume clamp method is based on adjusting the pressure of the pressure device 204 to keep the volume of the artery constant and thus keeping the amount of light that is detected by the PPG sensor 206 constant (at a target value), it is possible to compensate for the change in perfusion by decreasing the target value for the PPG signal by a factor y. Alternatively, the setpoint light intensity could be maintained at the same level and the calibration function ($BP_{final\_location}$ as a function of p) shifted downward instead. In another alternative, both the setpoint light intensity and the calibration function can be changed. The amount by which the setpoint is changed or the calibration function is shifted depends on the amount of change in perfusion. The same principle can be applied to a decrease in perfusion.

The relationship between changes in blood perfusion (which can be a percentage change x or some other measure of the magnitude of the change) and the corresponding factors by which the measured light intensity changes (y) and/or the calibration function changes can be determined and stored in the control unit to enable a recalculation of calibration constants (e.g. the target light intensity) to be performed quickly. In some embodiments the relationship between x and y is the same for all users, but in other embodiments the relationship can depend on one or more user-specific parameters, such as age, gender, ethnicity and skin tone of the user. In yet further embodiments, a user-specific relationship can be determined by the apparatus 200, for example by obtaining PPG measurements at different amounts of perfusion, which may, for example, be induced by the user deliberately putting a limb in cold or warm water (or into water at a range of different temperatures), by exercising, or with medication.

After the setpoint and calibration function have been determined (either by the full calibration/recalibration procedure or one in which the first step is reduced or skipped), the BP monitoring device 202 can measure the blood pressure $BP_{final\_location}$ conventionally by controlling the pressure p of the first pressure device 204 such that the light level measured by the PPG sensor 206 is kept constant at the setpoint, with the calibration function being used to calculate $BP_{final\_location}$ from p.

As described above, volume-clamp BP monitoring devices can be used to provide a continuous measure of the BP of a user. However, volume clamping a finger (or other part of the body) for a long period time (e.g. more than an hour) is uncomfortable and may have side effects, so it may be necessary to rest that body part for a period of time before resuming the BP measurements. As a result, volume-clamp BP monitoring devices are available that comprise a second cuff or other pressure device and associated PPG sensor that can be put on a different part of the body of the user and that can be used to measure the BP of the user from that body part while the first cuff (or other first pressure device) is deflated to rest the first part of the body. Example BP monitoring devices comprise two finger cuffs, and the monitoring device alternates between measuring the BP in the first finger and in the second finger.

Thus, in currently-available two-cuff volume-clamp BP monitoring devices, only one of the cuffs and the associated PPG sensor are used to measure the BP of the user at any given time. The other cuff is deflated and measurements from the associated PPG sensor are not used to determine the BP of the user.

Therefore, in a preferred embodiment, the invention described above is implemented in a two-pressure device volume-clamp BP monitoring device, and at any given time the PPG sensor that is not being used to measure the BP of the user is used to obtain the PPG signal that is analysed to determine a measure of blood perfusion in the user.

Figure 6:
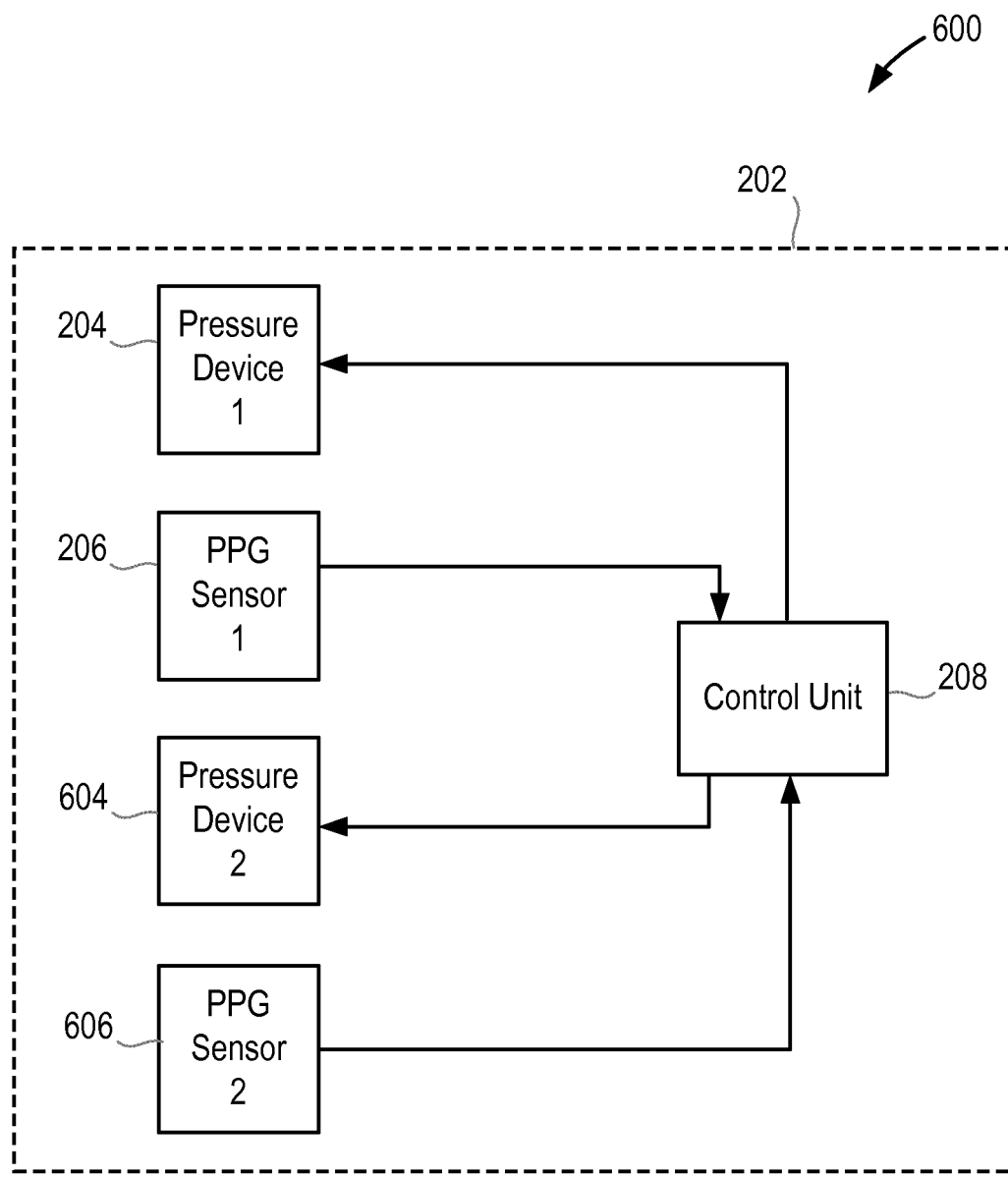
FIG. 6 shows an alternative apparatus according to a preferred embodiment.

FIG. 6 shows an apparatus according to the preferred embodiment. The apparatus 600 comprises a volume-clamp blood pressure monitoring device 202 as shown in FIG. 2. Thus the volume-clamp blood pressure monitoring device 202 comprises a first pressure device 204 (for example a cuff) and an associated first PPG sensor 206 that measures a PPG signal from the part of the body that the first pressure device 204 applies pressure to. The first pressure device 204 and first PPG sensor 206 are connected to a control unit 208.

In this preferred embodiment, the volume-clamp blood pressure monitoring device 202 further comprises a second pressure device 604 and a second PPG sensor 606 that are connected to the control unit 208. The second pressure device 604 is to be placed on or around a second part of the body of the user (e.g. a different finger to the first pressure device 204) and the second PPG sensor 606 measures a PPG signal from the second part of the body of the user. Preferably the second pressure device 604 and second PPG sensor 606 are of the same type as the first pressure device 204 and first PPG sensor 206 respectively (embodiments of which are described above with respect to FIG. 2).

The control unit 208 is configured to alternately measure the BP of the user using the first pressure device 204 and first PPG sensor 206 and measure the BP of the user using the second pressure device 604 and the second PPG sensor 606. That is, the BP monitoring device 202 applies pressure to the first body part using the first pressure device 204 and obtains a PPG signal using the first PPG sensor 206. The control unit 208 operates as described above with respect to FIGS. 2 and 3 to control the pressure applied by the first pressure device 204 to maintain the PPG signal measured by the first PPG sensor 206 at a constant level. At this time the second pressure device 604 and second PPG sensor 606 are not used to measure the BP of the user (so for example the second pressure device 604 will not be applying a significant pressure to the second part of the body of the user). Instead, and in accordance with this preferred embodiment, the second PPG sensor 606 is used to obtain a PPG signal from the second part of the body of the user, and this PPG signal is analysed by the control unit 208 to determine the measure of blood perfusion, and to determine whether to trigger a recalibration in response to a detected change in perfusion.

At a required time (for example after a predetermined interval or when some other criteria is met), the control unit 208 can switch to measuring the BP of the user using the second pressure device 604 and the second PPG sensor 606. That is, the BP monitoring device 202 applies pressure to the second body part using the second pressure device 604 and obtains a PPG signal using the second PPG sensor 606. The control unit 208 operates as described above with respect to FIGS. 2 and 3 to control the pressure applied by the second pressure device 604 to maintain the PPG signal measured by the second PPG sensor 606 at a constant level. At this time the first pressure device 204 and first PPG sensor 206 are not used to measure the BP of the user (so for example the first pressure device 204 will not be applying a significant pressure to the first part of the body of the user). Instead, and in accordance with this preferred embodiment, the first PPG sensor 206 is used to obtain a PPG signal from the first part of the body of the user, and this PPG signal is analysed by the control unit 208 to determine the measure of blood perfusion, and to determine whether to trigger a recalibration in response to a detected change in perfusion.

To get a good PPG signal with low noise, a PPG sensor must make good contact with the skin. Therefore, to improve the quality of the PPG signal that is obtained for the purposes of determining the blood perfusion, the pressure device associated with that PPG sensor can be used to apply pressure to the PPG sensor to improve the contact of that sensor with the skin while the other pressure device and PPG sensor are being used to measure the BP of the user.

Thus, in preferred embodiments where the pressure devices 204, 604 are cuffs, rather than completely deflate the first cuff 204 when the BP monitoring device 202 switches to using the second cuff 604 to measure BP, the control unit 208 partially deflates the first cuff 204 so that it still applies some pressure to the first PPG sensor 206 to provide the signal for measuring the blood perfusion. This partial deflation (which can also be viewed as a partial inflation from atmospheric pressure) allows the body part to rest and recover from the continuous pressure experienced during a BP measurement, while still allowing a good quality PPG signal to be obtained. The pressure applied by the pressure device 204, 604 should be high enough to make adequate contact between the PPG sensor and the body part, but low enough not to have any detrimental effect on hemodynamics or the comfort of the user. This might be achieved, for example, using a pressure of 5 to 15 mmHg, although it is envisaged that pressures outside this range might also be appropriate.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

In the claims it should be noted that "an apparatus for measuring blood pressure" and "a method for measuring blood pressure" do not necessarily imply that values for blood pressure are given as an output to the user or a caregiver, but it could also or alternatively be that the apparatus or a system using the method uses the pressure of the first pressure device 204 and/or the blood pressure associated with the pressure of the first pressure device 204 internally in the apparatus/system to derive (an)other haemodynamic/cardiovascular parameter(s) such as cardiac output, vascular resistance, arterial stiffness and stroke volume.

The invention claimed is:

1. An apparatus for measuring blood pressure (BP) of a user, the apparatus comprising:

a volume-clamp BP monitoring device that comprises a first pressure device that applies pressure to a first part of a body of the user, a first photoplethysmogram (PPG) sensor that obtains a first PPG signal from the first part of the body of the user, and a controller that analyzes the first PPG signal, control the pressure of the first pressure device to maintain the first PPG signal at a constant level, and to determine the BP of the user from the pressure of the first pressure device;

a second pressure device that applies pressure to a second part of the body of the user;

a second PPG sensor, separate from the first PPG sensor, that measures a physiological characteristic of the user in the second part of the body of the user, wherein the second part of the body is separate from the first part of the body;

wherein the apparatus:
alternately measures the BP of the user using the first pressure device and the first PPG sensor, and the second pressure device and the second PPG sensor;

analyzes the PPG signal from the second PPG sensor to determine a measure of the blood perfusion in the second part of the body of the user when the first pressure device and first PPG sensor are being used to measure the BP of the user in the first part of the body of the user;

analyzes the PPG signal from the first PPG sensor in to determine a measure of blood perfusion in the first part of the body of the user when the second pressure device and second PPG sensor are being used to measure the BP of the user in the second part of the body of the user; and determines whether to perform a recalibration of the volume-clamp BP monitoring device based on changes in one of: the blood perfusion measured in the first part of the body and the blood perfusion measured in the second part of the body.

2. The apparatus of claim 1, wherein the apparatus further uses the second pressure device to apply pressure to the second PPG sensor to contact the second PPG sensor with the second part of the body of the user when the first pressure device and the first PPG sensor are being used to measure the BP of the user; and uses the first pressure device to apply pressure to the first PPG sensor to contact the first PPG sensor with the first part of the body of the user when the second pressure device and the second PPG sensor are being used to measure the BP of the user.

3. The apparatus of claim 1, wherein the measure of blood perfusion is one or more of a DC value of the measured physiological characteristic, an amplitude of pulses in the measurements, and characteristics of a morphology of pulses in the measured physiological characteristic.

4. The apparatus of claim 1, wherein the measure of blood perfusion is a DC value of the measured physiological characteristic, and wherein the apparatus analyzes the measured physiological characteristic to determine the DC value in the measurements, and to determine whether to perform the recalibration of the volume-clamp blood pressure monitoring device based on changes in the determined DC value.

5. The apparatus of claim 1, wherein the measure of blood perfusion is an amplitude of pulses in the measurements, and wherein the apparatus analyzes the measured physiological characteristic to determine the amplitude of pulses in the measurements, and to determine whether to perform the recalibration of the volume-clamp blood pressure monitoring device based on changes in the amplitude of the pulses.

6. The apparatus of claim 1, wherein the measure of blood perfusion is a characteristic of a morphology of pulses in the measured physiological characteristic, and wherein the apparatus determines characteristics of the morphology of pulses in the measurements of the physiological characteristic, and to determine whether to perform the recalibration of the volume-clamp blood pressure monitoring device based on changes in the characteristics.

7. The apparatus of claim 1, wherein the controller executes the recalibration by (i) applying a range of pressures to the first body part using the first pressure device and obtaining a PPG signal using the first PPG sensor at multiple pressures in the range of pressures; (ii) analyzing the obtained PPG signals to select the constant level for the first PPG signal; and (iii) determining a calibration function that relates the pressure of the first pressure device to the BP of the user.

8. The apparatus of claim 7, wherein the range of pressures comprises pressures above and below the pressure of the first pressure device required to maintain the first PPG signal at the constant level.

9. The apparatus of claim 7, wherein the range of pressures comprises pressures above the pressure of the first pressure device required to maintain the first PPG signal at the constant level in an event that the blood perfusion has decreased, and the range of pressures comprises pressures below a pressure of the first pressure device previously required to maintain the first PPG signal at the constant level in the event that the blood perfusion has increased.

10. The apparatus of claim 9, wherein a minimum and/or maximum of a range of pressures are determined based on a magnitude of the change in blood perfusion.

11. The apparatus of claim 10, wherein the controller executes a recalibration by recalculating or scaling the constant level for the first PPG signal or recalculating or scaling one or more calibration constants in a calibration function that relates the pressure of the first pressure device to the BP of the user, wherein the recalculation or rescaling is based on the magnitude of the change in blood perfusion.

12. A non-transitory computer program product comprising a computer readable medium having computer readable code embodied therein, the computer readable code being configured such that, on execution by a suitable computer or processor, the computer or processor is caused to perform steps comprising:

applying pressure to a first part of a body of the user using a volume-clamp blood pressure (BP) monitoring device comprising a first pressure device;

obtaining a first PPG signal, via a first photoplethysmogram (PPG) sensor, from the first part of the body of the user;

analyzing the first PPG signal;

controlling the pressure of the first pressure device to maintain the first PPG signal at a constant level over time;

applying pressure to a second part of the body of the user using a second pressure sensor;

measuring a physiological characteristic of the user in the second part of the body of the user via a second PPG sensor that is separate from the first PPG sensor, wherein the second part of the body is separate from the first part of the body;

alternately measuring the blood pressure of the user using the first pressure device and the first PPG sensor, and the second pressure device and the second PPG sensor;

analyzing the PPG signal from the second PPG sensor to determine a measure of the blood perfusion in the second part of the body of the user when the first pressure device and first PPG sensor are being used to measure the BP of the user in the first part of the body of the user;

analyzing the PPG signal from the first PPG sensor in to determine a measure of the blood perfusion in the first part of the body of the user when the second pressure device and second PPG sensor are being used to measure the BP of the user in the second part of the body of the user; and determining whether to perform a recalibration of the volume-clamp BP monitoring device based on at least one of: changes in the measure of blood perfusion at the first part of the body and changes in the measure of blood perfusion at the second part of the body.

13. A method of measuring blood pressure (BP) of a user, the method comprising:
    applying pressure to a first part of a body of the user using a volume-clamp blood pressure (BP) monitoring device comprising a first pressure device;
    obtaining a first PPG signal, via a first photoplethysmogram (PPG) sensor, from the first part of the body of the user;
    analyzing the first PPG signal;
    controlling the pressure of the first pressure device to maintain the first PPG signal at a constant level over time;
    applying pressure to a second part of the body of the user using a second pressure sensor;
    measuring a physiological characteristic of the user in the second part of the body of the user via a second PPG sensor that is separate from the first PPG sensor, wherein the second part of the body is separate from the first part of the body;
    alternately measuring the blood pressure of the user using the first pressure device and the first PPG sensor, and the second pressure device and the second PPG sensor;
    analyzing the PPG signal from the second PPG sensor to determine a measure of the blood perfusion in the second part of the body of the user when the first pressure device and first PPG sensor are being used to measure the BP of the user in the first part of the body of the user;
    analyzing the PPG signal from the first PPG sensor in to determine a measure of the blood perfusion in the first part of the body of the user when the second pressure device and second PPG sensor are being used to measure the BP of the user in the second part of the body of the user; and
    determining whether to perform a recalibration of the volume-clamp BP monitoring device based on at least one of: changes in the measure of blood perfusion at the first part of the body and changes in the measure of blood perfusion at the second part of the body.

* * * * *